United States Patent [19]

Underwood

[11] Patent Number: 4,537,060
[45] Date of Patent: Aug. 27, 1985

[54] APPARATUS AND METHOD FOR MULTIAXIAL IMPACT TESTING OF MATERIALS

[75] Inventor: John D. Underwood, Wales, United Kingdom

[73] Assignee: Monsanto Europe, S.A., Brussels, Belgium

[21] Appl. No.: 562,921

[22] Filed: Dec. 19, 1983

[30] Foreign Application Priority Data

Dec. 23, 1982 [GB] United Kingdom ............... 8236587

[51] Int. Cl.³ .............................................. G01N 3/30
[52] U.S. Cl. ........................................ 73/12; 73/839
[58] Field of Search .................. 73/12, 82, 87, 821, 73/844, 813, 838, 839

[56] References Cited

U.S. PATENT DOCUMENTS

| | | | |
|---|---|---|---|
| 2,398,746 | 4/1946 | Kanter | 73/844 X |
| 2,422,317 | 6/1947 | Stock et al. | 73/12 |
| 3,365,938 | 1/1968 | Matsushita et al. | 73/791 |
| 4,313,337 | 2/1982 | Myint | 73/12 |

FOREIGN PATENT DOCUMENTS

2714195 10/1977 Fed. Rep. of Germany ........ 73/813

OTHER PUBLICATIONS

B. I. Verkin et al., "Apparatus for Impact Tests in the 1.5°–300° K. Temp Range", Ind. Lab. (USA), vol. 38, No. 11, pp. 1767–1769, Nov. 1972.

V. A. Matonis—"The Driven Dart Impact Tester for Plastics", Paper Presented at the Society of Plastics Engineers Meeting in Detroit, Michigan, Nov. 1974.

T. Casiraghi et al., "New Developments in the Assessment of Impact Resistance Evaluation by Falling Weight Method", Plastics and Rubber Processing and Applications, vol. 2, No. 4, 1982.

*Primary Examiner*—Charles A. Ruehl
*Attorney, Agent, or Firm*—Gordon B. Seward

[57] ABSTRACT

A sample of material is tested by rupture with an impact member, relative movement of the sample and member being maintained at a substantially constant velocity along a straight line before and after impact and being derived from angular movement of a cam driven by a flywheel. The apparatus is capable of automatic operation (including automatic result recording) with increased operator safety, gives results of good reproducibility, and is quieter in use than previously proposed apparatus.

11 Claims, 8 Drawing Figures

APPARATUS AND METHOD FOR MULTIAXIAL IMPACT TESTING OF MATERIALS

BACKGROUND OF THE INVENTION

This invention relates to apparatus and methods for testing of materials, and particularly to such apparatus and method for testing the multiaxial impact strengths of materials.

An important criterion in the selection of materials, for example plastics materials, for use in any given application is the resistance of such materials to physical impacts. It is necessary to be able to test plastics materials in as reproducible a way as possible, particularly as a method of control in manufacture. For the latter purpose it is also desirable that testing be carried out quickly so that any tendency for the product to depart from the desired specification can be detected and corrected as soon as possible, and the results should also be reproducible. It is also desirable that the apparatus should be capable of carrying out a series of tests, and recording the results, automatically.

A distinction is to be drawn between uniaxial and multiaxial impact testing, an example of the former being the well-known Izod method wherein a notched bar of the material under test is clamped at one end and struck by a weighted pendulum so that such bars always break in the same direction. In a multiaxial impact test, on the other hand, no attempt is made to induce the direction of failure and the sample breaks in its weakest direction. It is believed that multiaxial impact testing is more representative of the way in which actual articles fail as a result of impacts experienced in use.

The most generally used type of apparatus for multiaxial impact testing involves the use of a dart to which weights are attached and which is allowed to fall from a height on to a sample of the material to be tested. Depending on whether or not the sample breaks as a result of this treatment, weights are either added to or removed from the dart until a weight is found which is just sufficient to break a statistically significant number of samples. Alternatively, the height of fall can be adjusted to achieve the same result. Since this method necessarily involves considerable operator time, not only in carrying out the tests themselves but also in preparing a sufficient number of samples, efforts have been made to devise a test that does not suffer from these disadvantages. As a result of such efforts, testing apparatus has been proposed that would measure the force exerted on the sample by the falling dart by means of an appropriate transducer placed beneath the sample or on the dart, the signals from the transducer being processed by a computer so that the instrument can provide a direct readout of the energy necessary to break that particular sample.

Examples of impact testing apparatus that have been designed in accordance with the foregoing proposals have, however, still suffered from the disadvantages that they consume many samples and are not automatic in operation. They require that an operator position each sample by hand, raise the dart and, after fall, remove the broken sample before repeating the test on another sample. They are noisy and there is also the danger of personal injury to the operator or damage to the apparatus if the weight is allowed to fall prematurely. Because of their size and the need for frequent operator access, it is not practical to enclose such apparatus so as to reduce noise or increase safety. It has been proposed to employ a dart driven by mechanical means rather than accelerated by gravity. According to that proposal, energy stored in a flywheel was applied to a dart through a crank on a shaft coupled to the flywheel by means of a clutch. Only a small portion of the crank's throw was utilizable, because of non-linearity problems, and the apparatus, although representing an advance in the art, was still large and somewhat noisy and did not gain general commercial acceptance. It has also been proposed to use a dart driven by servo-controlled hydraulic means.

SUMMARY OF THE INVENTION

A new impact-testing apparatus has now been developed that is capable of automatic operation (including automatic result recording) with increased operator safety, gives results of good reproducibility and is moreover much quieter in use than previously proposed apparatus. The apparatus can also be of such a small physical size that it can readily be enclosed so as to reduce noise and operational hazards even more.

The apparatus of the invention is one for multiaxial impact-testing of a material, comprising an impact member arranged for impact with a sample of the material, wherein either the energy or the force required to rupture the sample in its weakest direction on such impact is employed as a measure of the multiaxial impact strength of the material, characterized in that relative movement of the sample and the member is maintained at a substantially constant velocity along a straight line before and after impact and is derived from angular movement of a cam driven by a flywheel.

BRIEF DESCRIPTION OF THE DRAWINGS

An example of an apparatus according to the invention will now be described with reference to the accompanying Drawings, in which.

DETAILED DESCRIPTION

Figure 1:
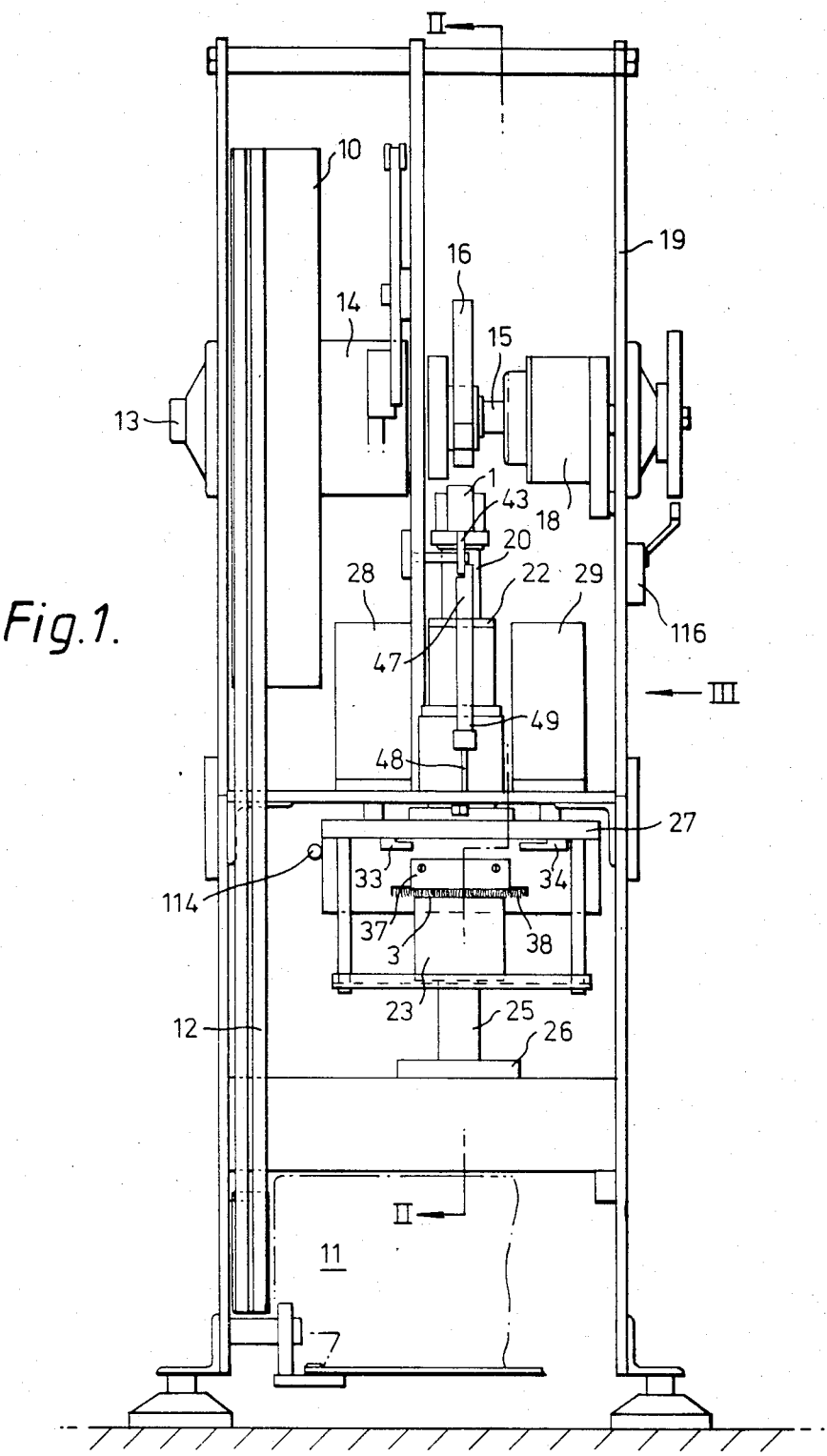
FIG. 1 is a side elevational view of the apparatus (with certain parts removed for clarity).
Figure 2:
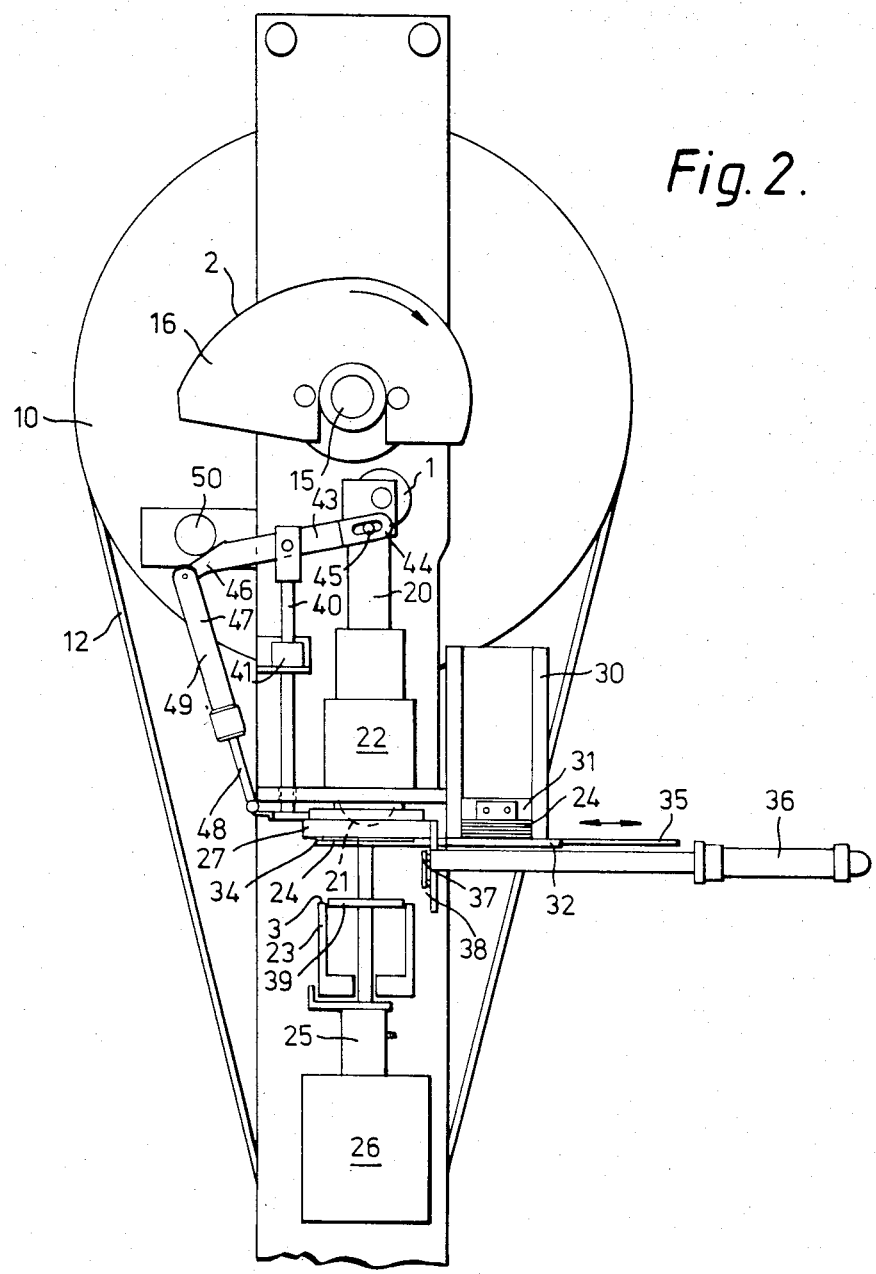
FIG. 2 is a part-sectional view along the line II—II in FIG. 1.

Referring to FIGS. 1 and 2, the apparatus comprises a flywheel 10 rotated by a motor 11 by means of a belt 12. The flywheel is mounted on a first shaft 13 connected via a single-revolution clutch 14 to a second shaft 15. The single-revolution clutch is a commercially available component (for example Borg Warner Type ETK 30) designed to engage for one complete revolution and then disengage. On shaft 15 there are mounted a cam 16, a sequence cam 17 (whose function will be described in a later paragraph dealing with control of the apparatus) and a free wheel 18 attached to a solid support 19 so that the shaft 15 can rotate in one direction only. The shape of the profile of the cam 16 can be seen in FIG. 2; it is designed so that the radius of the profile varies linearly with angle, for an arc 2 subtending an angle of 60° at the cam centre. Beneath the cam 16 is an impact member comprising a dart 20 having a hemispherical lower end 21 and at its upper end a roller 1 intended to reduce friction with the cam 16. The dart can slide vertically in guides 22, and rotation of the cam 16 in the direction permitted by the free-wheel 18 will force it downwards by means of arc 2 acting on roller 1.

Positioned below the dart 20 is a sample support 23 having an apertured top surface 3 of a shape corresponding to the borders of a sample 24, the sample being in the form of a plaque of the material to be impact tested. The support 23 is itself supported on a load cell 25 which is in turn mounted on a fixed load cell support 26. A clamp plate 27 that can be raised or lowered by the action of pneumatic cylinders 28 and 29 is arranged so as to clamp sample 24 against support 23.

Figure 4:
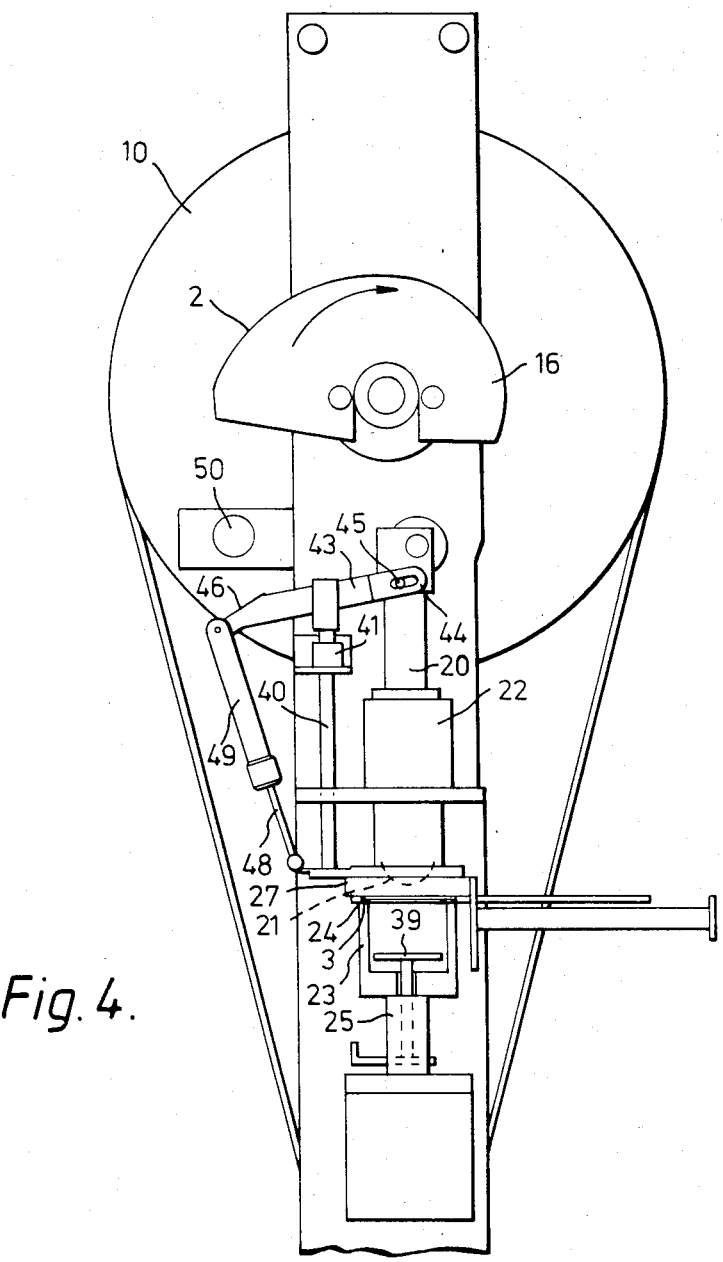
FIG. 4 is a part sectional view similar to FIG. 2 but showing the relative positions of the parts at a different stage in the testing sequence.
Figure 5:
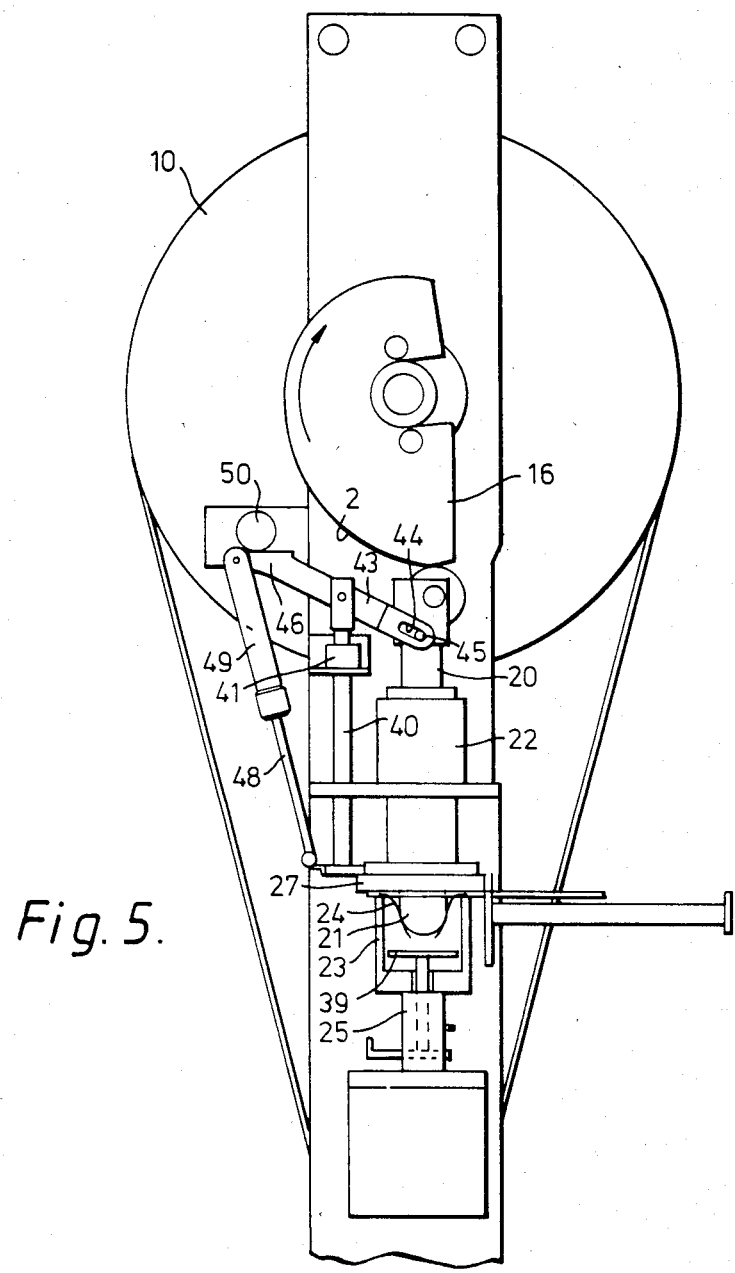
FIG. 5 is another part sectional view similar to FIGS. 2 and 4 but showing the relative positions of the parts at a third stage in the testing sequence.

A sample feed and ejection mechanism comprises a magazine 30 in which can be placed a vertical stack of samples 24 beneath a weight 31. The bottom sample of the stack rests on a feed tray 32, and both tray and magazine are fastened to the clamp plate 27. Fastened to the underside of the clamp plate 27 are two guides 33 and 34 shaped as shown, and the lowermost sample of the stack can slide horizontally on the feed tray and thence on to these guides. A feed ram 35, powered by pneumatic cylinder 36, is arranged so as to effect this sliding movement. A horizontally operating sample ejector 37 is arranged to move together with ram 35 and carries a brush 38 on its lower edge. An upwardly operating sample ejector 39 is arranged so as to penetrate the aperture of the sample support 23 and is also fastened to the clamp plate 27. All the parts 30 to 39 thus move up or down with the clamp plate 27. Referring to FIGS. 2, 4, 5, a dart ejector mechanism comprises a vertical push rod 40 slidable in a guide 41, fixed at its lower end to clamp plate 27 and having at its upper end a pivot on which is pivoted a dart ejector 43. One end 44 of the dart ejector is forked and the forks respectively have slots engaging with pins (one shown at 45) projecting horizontally from the upper end of the dart 20. The other end 46 of the dart ejector 43 is pivoted at the top of a damper 47, the lower end of which is fastened to clamp plate 27. Damper 47 consists of a rod 48 slidable within a tube 49, there being light friction elements (not shown) within the tube 49 so that the rod 48 is held against a small force but can slide axially within the tube under the influence of a larger force. Upward movement of the end 46 of the dart ejector 43 is limited by a fixed stop 50.

Figure 3:
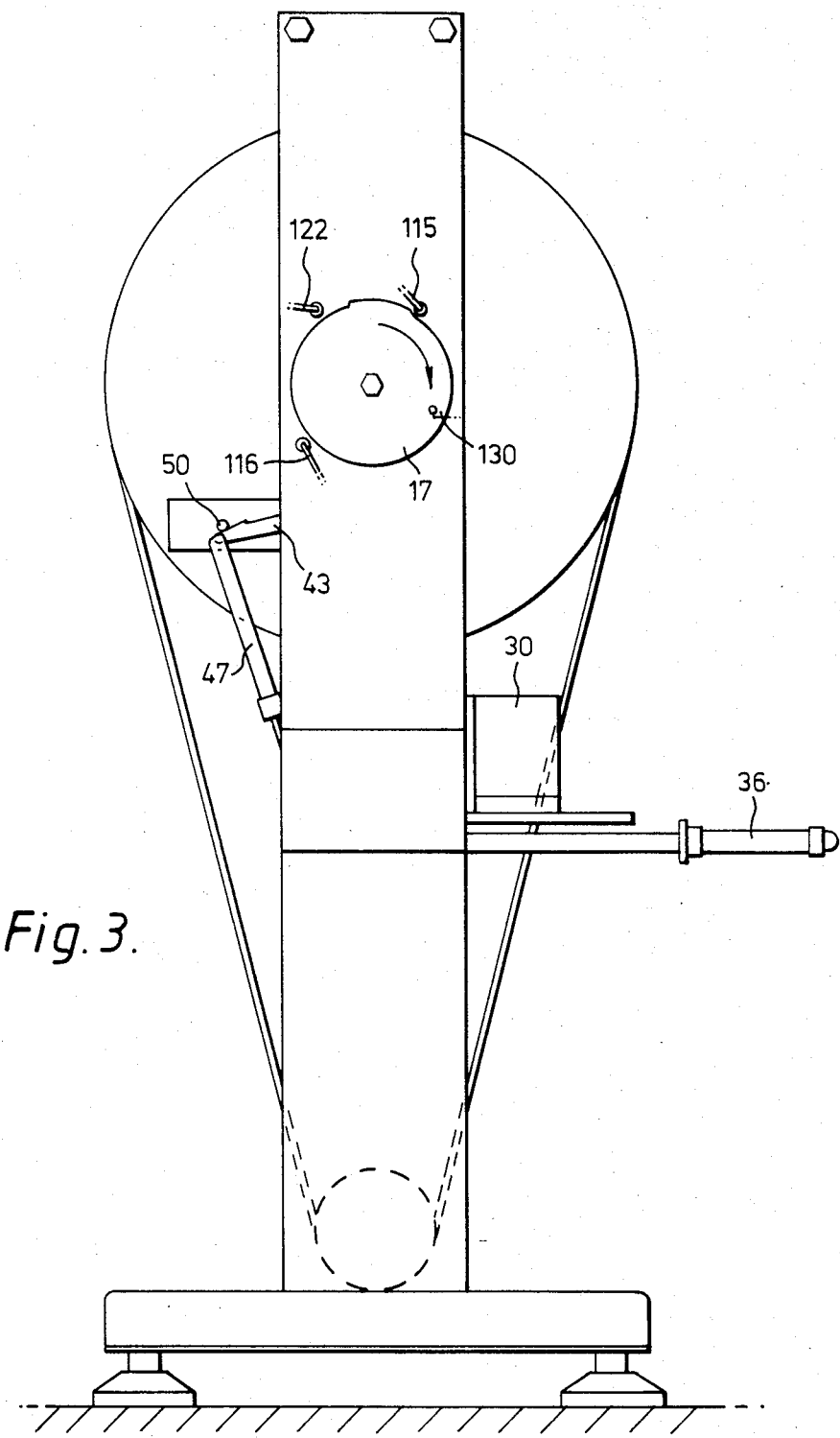
FIG. 3 is a side elevational view of the apparatus looking in the direction of the arrow III in FIG. 1.

Mechanically, the apparatus operates as follows. (Control components will be described later). The motor 11 is started and allowed to run the flywheel up to a steady speed. With the clamp plate 27 and dart 20 in their raised positions and the feed ram 35 positioned to the right as seen in FIGS. 3 to 5, a stack of samples is placed in the magazine 30 and the weight 31 placed on top. The feed ram moves to the left so that one sample is pushed along the feed tray 32 on to the guides 33 and 34, and the feed ram moves back to its original position. The clamp plate 27 then moves downwards so that the sample is clamped by its borders between clamp plate 27 and support 23. After a delay of a few seconds to allow the clamping force to reach a maximum, the clutch 14 is engaged so that cam 16 rotates, forcing the dart downwards on to the sample at a constant velocity so that the sample is broken, and producing from the load cell a signal dependent on the force acting on the sample. As the dart moves down, dart ejector 43 pivots on unnumbered pivot at the upper end of push rod 40. Further rotation of the cam brings the cam out of contact with roller 1, while movement of the dart is arrested when the end of 46 of dart ejector 43 contacts the stop 50.

The clamp plate 27 then moves upwards, and push rod 40 pushes up the dart ejector 43, which pivots against the stop 50 so that the end 44 is raised together with the dart 20. At the same time, the upwardly-operating sample ejector pushes the broken sample (which has been freed by opening of the clamp) up into the path of the horizontally operating sample ejector 37, subsequent leftwards movement of which (together with the sweeping action of brush 38) completes the ejection of the broken sample. Such leftwards movement is coincident with the feeding of a new sample from the magazine on to the guides 33 and 34, and the sequence is then repeated until no samples are left in the magazine. The absence of a sample on the feed tray 32 is detected by the control system, which blocks operation of the feed ram 35, and operation stops.

Figure 6:
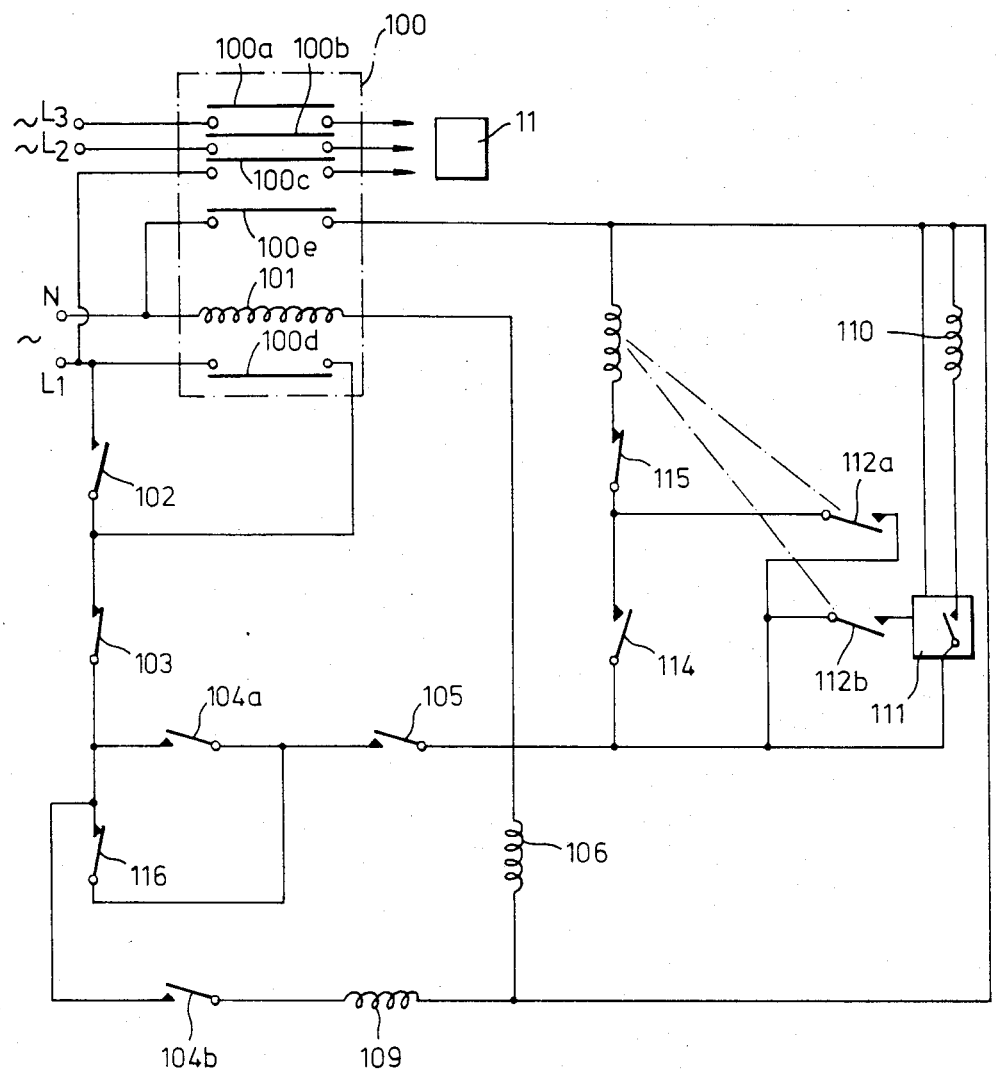
FIGS. 6 and 7 respectively show electric and pneumatic control circuits for use in controlling the apparatus shown in FIGS. 1 to 5.
Figure 7:
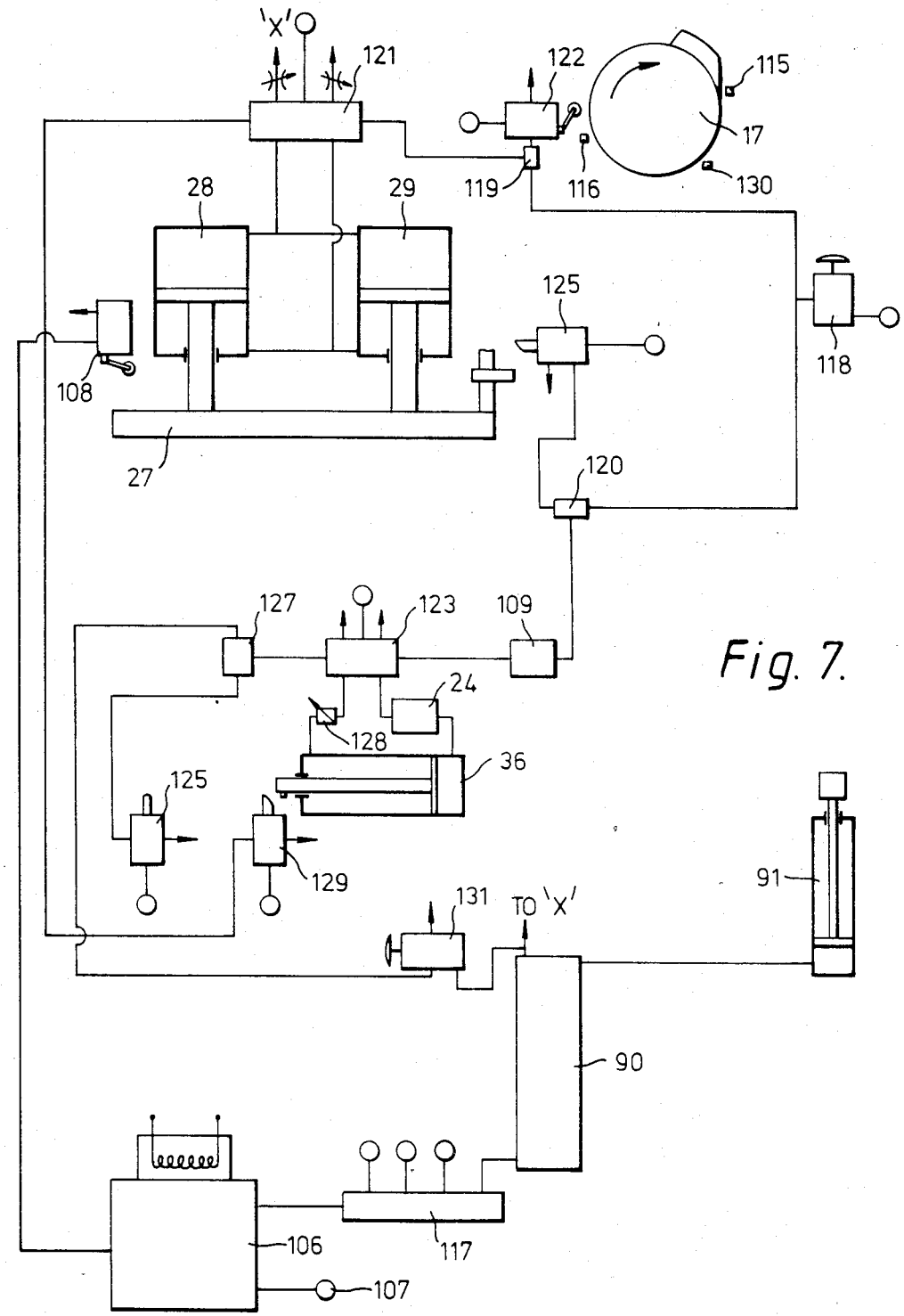

The control system is partly electric and partly pneumatic. In particular, as described above, pneumatic cylinders are employed to raise and lower the clamp plate 27 and to operate the feed ram 35. FIG. 6 shows the electrical circuit. The pneunatic circuit diagram is shown in FIG. 7, in which the clamp plate cylinders, the feed ram cylinder and the sequence cam are shown schematically.

The control circuits incorporate safety features designed to minimize the risk of injury to the operator or damage to the apparatus itself. Thus, for example, the apparatus as a whole is in normal use enclosed by a housing (not shown) and access can only be achieved through a door having a lock that is normally held closed by a pneumatic cylinder and that can be opened only as a result of exhaustion of the main air supply to the atmosphere. Consequently, no movement of the clamp plate or feed ram, nor engagement of the clutch, which all require compressed air, is possible whilst the door is unlocked. The door also incorporates a switch so that all electrical circuits are switched off if the door is opened.

Considering first the electrical circuit shown in FIG. 6, a three-phase mains supply has neutral terminal N and live terminals $L_1$, $L_2$ and $L_3$ which feed the motor 11 via normally-open contacts 100a, 100b and 100c of a relay 100. The coil 101 of relay 100 is energised by the closure of normally-open push-button start switch 102, normally-closed push-button stop switch 103, half 104a of a two-pole normally-open magazine switch 104 (closed by the presence of a sample 24 in magazine 30) and normally open door switch 105 (closed by shutting an operator-access door—not shown—in an apparatus housing). Contacts 100d of the relay 100, in parallel with start switch 102, are provided to override start switch 102 after the push button of the latter has been released.

Closure of switches 102 (or contacts $100_d$), 103, 104 and 105 also energises main air supply solenoid valve 106 (FIGS. 6 and 7), admitting compressed air from supply 107 to the pneumatic control system. The pneumatic system is exhausted to atmosphere via valve 108 (FIG. 7) when valve 106 is de-energised. Valve 108 is activated by movement of the clamp plate 27 and prevents such exhaustion unless the clamp plate is fully raised.

Contacts 100e of relay 100 (FIG. 6) connect the mains neutral terminal N to the return end of the coil of main air supply solenoid valve 106 and to other parts of the electrical circuit described below.

Closure of the second half 104b of magazine switch 104 opens solenoid valve 109. As will be explained, the function of solenoid valve 109 is to prevent sample-feeding motion when the magazine is empty. The single revolution clutch 14 (FIG. 1) is pneumatically controlled by means of a cylinder (not shown) and a solenoid valve of which only the energising coil 110 is shown (FIG. 6). When coil 110 is momentarily energised, the clutch is engaged; engagement is maintained mechanically until cam 16 completes one revolution, and the clutch then disengages itself. Coil 110 is fed via the contacts of a variable timer 111 whose function is to provide the few seconds' delay referred to above between downward movement of the clamp plate 27 and engagement of the clutch 14. Initiation of the time is effected by closure of one set of normally-open contacts 112a of timer relay 112, the coil of which is energised through normally-open timer start switch 114 (closed when clamp plate 27 is at its lowest position) and normally-closed sequence-cam-operated switch 115. A second set of normally-open contacts 112b of timer relay 112 maintains the relay in an energised state after the timer start switch 114 has reopened until the sequence-cam-operated switch 115 opens.

A second sequence-cam-operated normally-closed switch 116 is placed in parallel with contacts 104a of the magazine switch 104. Its function as an automatic stop switch will be explained later.

Turning now to the pneumatic system shown in FIG. 7, air from the main supply valve 106 enters a manifold 117 supplying a reservoir 90 and various other parts of the system as shown, including door-locking cylinder 91. A push-button start valve 118 admits air from manifold 117 to two-way shuttle valves 119 and 120 when its button is pressed, or exhausts them when its button is released. Pressing this button thus causes a pneumatic signal to be transmitted via a first input of a shuttle valve 119 to a first input of a clamp control valve 121, resulting in air being admitted from reservoir 90 to the lower sides of clamp cylinders 28 and 29 and exhausting their upper sides to atmosphere, ensuring that the clamp plate 27 and dart 20 are both fully raised. The other input of shuttle valve 119 is connected to a valve 122 operated by the sequence cam 17. The exhaust ports of control valve 121 are fitted with throttles so as to prevent too sudden a movement of the clamp plate 27 either up or down.

Pressing the button of start valve 118 also causes a signal to be transmitted via shuttle valve 120 and solenoid valve 109 to a sample-feed control valve 123, resulting in air being admitted via a time delay 124 to the right hand side of sample feed cylinder 36. The other input of shuttle valve 120 is connected to a pilot valve 125 opened by upward movement of clamp plate 27 close to the latter's fully raised position. (Pilot valve 125 is only operated by upward movement of clamp plate 27. Downward movement has no effect). The function of time delay 124 is to ensure that clamp 27 is fully raised before operation of the feed ram 35, the latter being relatively fast compared with that of the clamp. Thus, either the action of pushing the start button of valve 118 or the approach of clamp plate 27 to its upper limit of travel will result in a sample (if there is one in the magazine) being fed on to the guides 33 and 34. If there is no sample left in the magazine, solenoid valve 109 remains closed and there is no feeding movement.

Leftward approach of ram 35 towards its fullest extent operates pilot valve 125 causing the transmission of a signal via two-way shuttle valve 127 to a second input of sample-feed control valve 123; this exhausts air from the right-hand side of sample feed cylinder 36 and admits air to the left-hand side via a speed-controlling throttle valve 128, causing the ram 35 to move back again to the right. When ram 35 approaches its fullest extent to the right, it operates a pilot valve 129 thus causing a signal to be transmitted to a second input of clamp control valve 121, resulting in exhaustion of the lower sides of cylinders 28 and 29 and admission of air to their upper sides with consequent downward movement of clamp plate 27 on to the sample, clamping it against the support 23. When clamp 27 is fully lowered, it closes timer start switch 114 (FIG. 6), so initiating operating of timer 111 and subsequent engagement of clutch 14 and downward movement of dart 20.

As the sequence cam 17 rotates, it successively causes:

a. Opening of switch 115, thus causing the timer relay 112 to be de-energised;
b. Closing of a data-recording trigger switch 130; this causes data-recording equipment (not shown) to accept the electrical output of the load cell 25, spurious outputs produced during closure of the clamp and initial acceleration of the dart being thereby suppressed until switch 130 closes;
c. Opening of the normally-closed switch 116; unless this switch is over-ridden by the closure of magazine switch contacts 104a as a result of the presence of a sample in the magazine, such opening de-energises the main relay 100 and thus switches off the whole apparatus;
d. Opening of pilot valve 122 so as to pass a pneumatic signal to the "clamp open" input of clamp control valve 121, thus either initiating another test cycle or (where no samples remain and magazine switch contacts 104a are open) exhausting the pneumatic system through main air supply valve 106 and valve 108.

A push button operated valve 131 is provided whereby a pneumatic signal can be applied to the second input of two-way shuttle valve 127. Pressing its button results in right-ward movement of sample feed ram 35. This is useful as a means of withdrawing the feed ram should an incorrectly shaped sample jam in the guides 33 and 34. If the main relay 100 is then de-energised by means of the stop switch 103, the motor stops and air exhausts from the pneumatic system so that the door can be opened and the jammed sample cleared by hand.

The relative velocity of the dart and sample is substantially constant before and after impact; the relative velocity is usually chosen with a view to simulating actual impact conditions of an article in service. For example, for testing plastics materials intended for use in the manufacture of automobile bumpers (fenders), appropriate velocities are 2.23 m/sec (5 miles per hour) or 6.7 m/sec (15 miles per hour).

The speed and weight of the flywheel are not critical provided it has sufficient momentum that there be substantially no deceleration on impact. For example, a 30 kilogram flywheel of diameter 0.35 meter rotating at 340 revolutions per minute has been found satisfactory where the operative arc of the cam profile subtends an angle of 60 to 90° at the cam centre. Because the action of the cam can extend over a substantial angle of the cam's rotation, it is possible to use a relatively small and light flywheel, thus reducing the size and cost of the apparatus and facilitating enclosure, as mentioned above.

Figure 8:
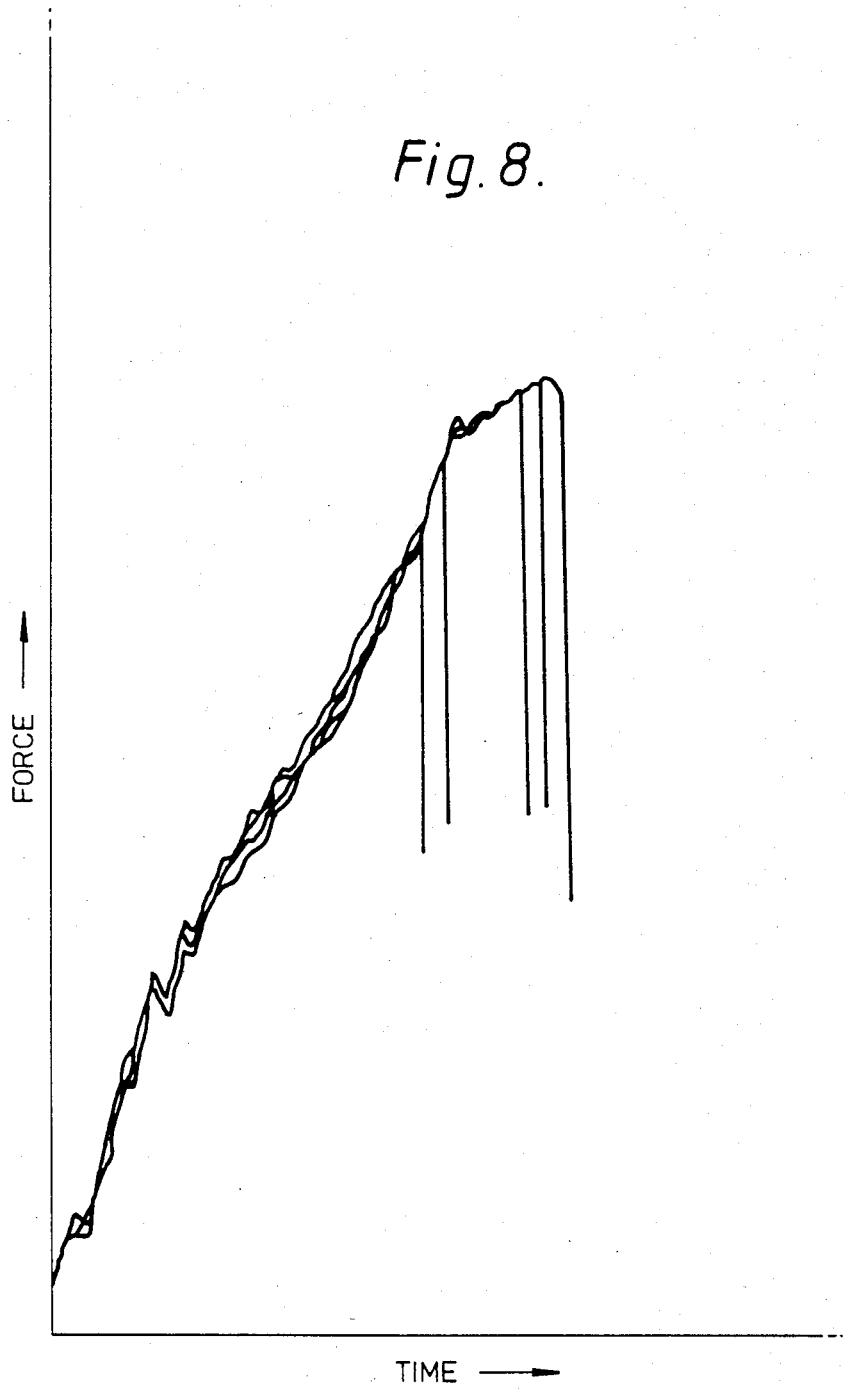
FIG. 8 shows a typical series of graphs of force against time obtained by testing a sequence of samples of the same material in the apparatus.

The output of the load cell can be used in any appropriate manner to provide data concerning the impact resistance of the sample under test. FIG. 8 shows typical graphs of force against time being superimposed traces obtained by testing a succession of samples of the same material. Such graphs may be obtained by photographing oscilloscope traces but it is more convenient to convert the load cell output to digital form that can be processed in a computer to give the required data. For example, simply the maximum force exerted on the sample by the dart may be recorded, or preferably the force is integrated with respect to time between the limits corresponding to zero and maximum force. This integral, since the relative velocity of sample and dart is substantially constant, can be used as a comparative measure of the energy required to break the sample. The computer can also be used to provide a plot of such data on graph paper, although it is in any event useful to be able to display the load cell output on a storage oscilloscope so that the performance of the apparatus can readily be monitored if desired whilst tests are in progress.

Instead of the electropneumatic control system described above, the apparatus can be controlled by other means such as for example a microcomputer controlling motors powering the clutch engagement and clamp plate and sample feed motions.

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. Apparatus for multiaxial impact-testing of a material, comprising an impact member arranged for impact with a sample of the material, wherein either the energy or the force required to rupture the sample in its weakest direction on such impact is employed as a measure of the multiaxial impact strength of the material, characterized in that relative movement of the sample and the member is maintained at a substantially constant velocity along a straight line before and after impact and is derived from angular movement of a cam driven by a flywheel.

2. Apparatus according to claim 1, comprising means for measuring the time integral of the force exerted on the sample by the impact member from the time of first contact of the impact member with the sample to the time when the said force reaches a maximum.

3. Apparatus according to either claim 1 or claim 2, in which the cam is shaped so that the said relative movement of the sample and impact member is maintained while the cam moves though an angle of between 45° and 270°.

4. Apparatus according to claim 3, comprising a single revolution clutch coupling the cam to the flywheel.

5. Apparatus according to claim 4, comprising a clamp for clamping the borders of the sample, and timer control means whereby engagement of the clutch is consequent on closure of the clamp.

6. Apparatus according to claim 5, comprising means for delaying engagement of the clutch after closure of the clamp.

7. Apparatus according to claim 5, in which a number of samples can be tested sequentially, comprising sample ejection means and means for successively advancing the samples into position for clamping and for impact with the impact member, such advancement taking place simultaneously with or immediately after ejection of the broken preceding sample.

8. Apparatus according to claim 5, wherein the clamp is such as to hold the sample stationary and the action of the cam is such as to drive the impact member towards the sample.

9. Apparatus according to claim 5, in which separation of the impact member from a sample after impact with that sample occurs substantially simultaneously with opening of the clamp.

10. Apparatus according to claim 7, comprising means for recording energy or force and system control means whereby the following operations automatically take place in sequence:
  (a) The sample clamp opens;
  (b) One sample is moved into position in the clamp and the broken preceding sample is ejected from the clamp;
  (c) The clamp closes and clamps the borders of the sample;
  (d) The clutch is engaged and the cam makes its angular movement, causing the impact member to impact the sample;
  (e) The energy or force required to rupture the sample is recorded;
  (f) The cam continues its angular movement until one revolution has been completed;
  (g) The clutch is disengaged and angular movement of the cam ceases;
  (h) The clamp opens and the impact member is withdrawn;
  (i) Operations (a) to (g) are repeated until all samples have been impacted; and
  (j) Operation stops.

11. A method for multiaxial impacting testing of a material, in which there is employed an apparatus according to claim 1.

* * * * *